US006399355B1

(12) United States Patent
Kwong et al.

(10) Patent No.: US 6,399,355 B1
(45) Date of Patent: *Jun. 4, 2002

(54) NON-NATURALLY OCCURRING TARGETED LIPOLYTIC COMPOUNDS AND RELATED COMPOSITIONS AND METHODS

(75) Inventors: Peter D. Kwong, New York; Wayne A. Hendrickson, Hastings on Hudson, both of NY (US)

(73) Assignee: The Trustees of Columbia University in the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/483,228

(22) Filed: Jun. 7, 1995

(51) Int. Cl.[7] ................................. C12N 7/06

(52) U.S. Cl. ..................... 435/238; 435/177; 435/195; 435/236

(58) Field of Search ................. 435/198, 69.1, 435/172.1, 195, 320.1, 252.3, 240.2, 235.1, 255, 238, 174, 177, 236; 536/27; 935/14; 530/387.9, 388.26, 389.1, 350; 424/450, 94.6, 94.61, 94.63

(56) References Cited

U.S. PATENT DOCUMENTS

| | | | |
|---|---|---|---|
| 5,019,508 A | * 5/1991 | Johnson et al. | ............. 435/198 |
| 5,130,130 A | 7/1992 | Menez et al. | |
| 5,178,864 A | 1/1993 | Lees et al. | |
| 5,232,911 A | 8/1993 | Vidal | |
| 5,298,420 A | 3/1994 | Chang | |
| 5,342,924 A | 8/1994 | Chang | |
| 5,552,530 A | * 9/1996 | Johnson et al. | .......... 530/387.9 |
| 5,718,915 A | * 2/1998 | Virtanen et al. | ............ 424/450 |
| 5,961,973 A | * 10/1999 | Crea | ....................... 424/133.1 |
| 6,287,561 B1 | * 9/2001 | Crea | ....................... 424/133.1 |

FOREIGN PATENT DOCUMENTS

WO    WO 93/18162    * 9/1993

OTHER PUBLICATIONS

Ruffini et al. "B–Bungarotoxin–Mediated Liposome Fusion: Spectroscopic Characterization by Fluorescent and ESR". Biochemistry, vol. 29:9644–9651, 1990.*
Kreitman et al. "Targeting Growth Factor Receptors with Fusion Toxins". Intl. J. Immunopharmac., vol. 14, No. 3:465–472, 1992.*
Lozano et al. "Thioredoxin–Linked Reductive Inactivation of Venom Neurotoxins". Archives of Biochemistry and Biophysics, vol. 309, No. 2:356–362, 1994.*
Ashorn, P., et al. (1990) "Elimination of infectious human immunodeficiency virus from human T–cell cultures by synergistic action of CD4–Pseudomonas exotoxin and reverse transcriptase inhibitors." *Proc. Natl. Acad. Sci., USA* 87:8889–8893 (Exhibit 2).
Ashorn, P., et al., (1991) "Anti–HIV activity of CD4–Pseudomonas exotoxin on infected primary human lymphocytes and monocyte/macrophages." *J. Infect. Dis.* 163: 703–709 (Exhibit 3).
Dennis, E.A. (1994) "Diversity of group types, regulation, and function of phospholipase $A_2$." *J. Biol. Chem.* 269: 13057–13060 (Exhibit 4).
Djkstra, B.W., et al., (1981) "Structure of bovine pancreatic phospholipase $A_2$ at 1.7 Å resolution." *J. Mol. Biol.* 147: 97–123 (Exhibit 5).
Fitzgerald, D. and I. Pastan (1989) "Targeted toxin therapy for the treatment of cancer." *J. Natl. Cancer Inst.* 81: 1455–1463 (Exhibit 6).
Kondo, K. et al., (1982) "Amino acid sequence of $\beta_2$–bungarotoxin from *Bungarus multicinctus* venom. The amino acid substitutions in the B chains." *J. Biochem.* 91: 1519–1530 (Exhibit 7).
Kondo, K., et al. (1982) "Amino acid sequences of three β–bungarotoxins ($\beta_3$–, $\beta_4$–, $\beta_5$–bungarotoxin) from *Bungarus multicinctus* venom. Amino acid substitutions in the A chains." *J. Biochem* 91: 1531–1548 (Exhibit 8).
Kwong. P., et al. (1989) "β–Bungarotoxin." *J. Biol. Chem.* 264: 19349–19353. (Exhibit 9).
Pastan, I., et al. (1992) "Recombinant toxins as novel therapeutic agents." *Annu. Rev. Biochem.* 61: 331–354 (Exhibit 10).
Press, O. W. (1991) "Immunotoxins." *Biotherapy* 3: 65–76 (Exhibit 11).
Radvanyi, F., et al. (1987) "The interaction between the presynaptic phospholipase neurotoxins β–bungarotoxin and crotoxin and mixed detergent–phosphatidylcholine micelles." *J. Biol. Chem.* 262: 8966–8974 (Exhibit 12).
Scott, D. L., et al. (1990) "Interfacial catalysis: the mechanism of phospholipase $A_2$." *Science* 250: 1541–1546 (Exhibit 13).
Siegall, C.B. (1994) "Targeted toxins as anticancer agents." *Cancer* 74: 1006–1012 (Exhibit 14).

(List continued on next page.)

*Primary Examiner*—Donna C. Wortman
(74) *Attorney, Agent, or Firm*—John P. White; Cooper & Dunham LLP

(57) ABSTRACT

This invention provides a non-naturally occurring targeted lipolytic compound comprising a lipolytic agent linked to a targeting agent. In an embodiment, the lipolytic agent is covalently attached to the targeting agent. In an embodiment, the lipolytic agent is a phospholipase and the targeting agent is a viral receptor. This invention further provides for therapeutic uses of the non-naturally occurring targeted lipolytic compound. In an embodiment, the non-naturally occurring targeted lipolytic compound neutralizes virions of the human immunodeficiency virus (HIV).

2 Claims, 6 Drawing Sheets

OTHER PUBLICATIONS

Vernon, L.P. and J.D. Bell (1992) "Membrane structure, toxins and phospholipase $A_2$ activity." *Pharmac. Ther.* 54: 269–295 (Exhibit 15).

Westerlund B., et al. (1992) "The three–dimensional structure of notexin a presynaptic neurotoxic phospholipase $A_2$ at 2.0 Å resolution." *Fed. Eur. Biochem. Soc.* 301: 159–164 (Exhibit 16).

* cited by examiner

FIGURE 1.1
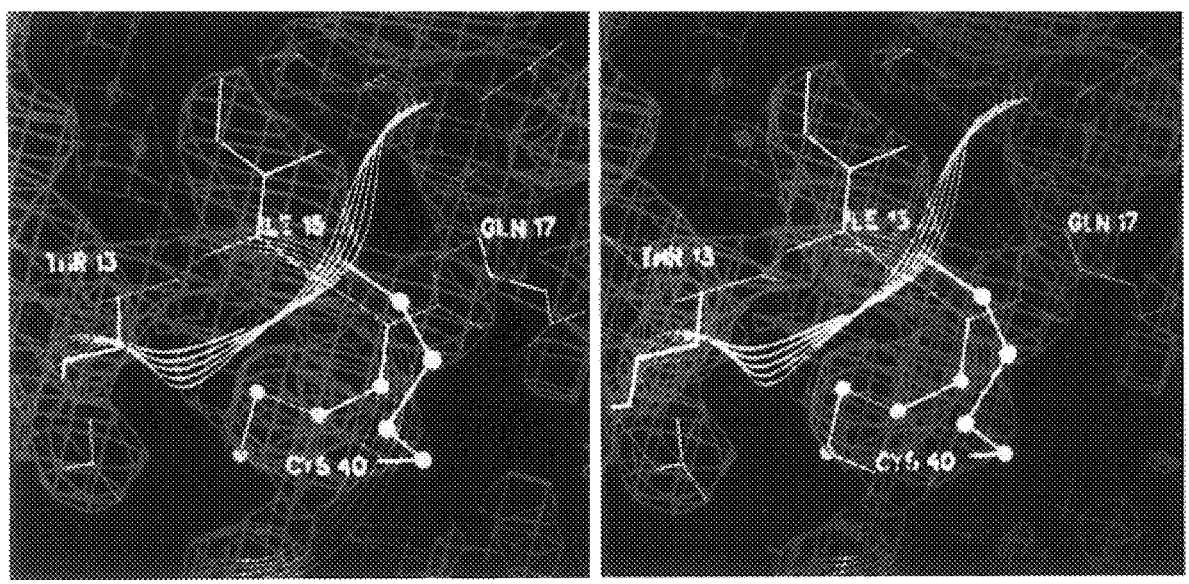

FIGURE 1.2A
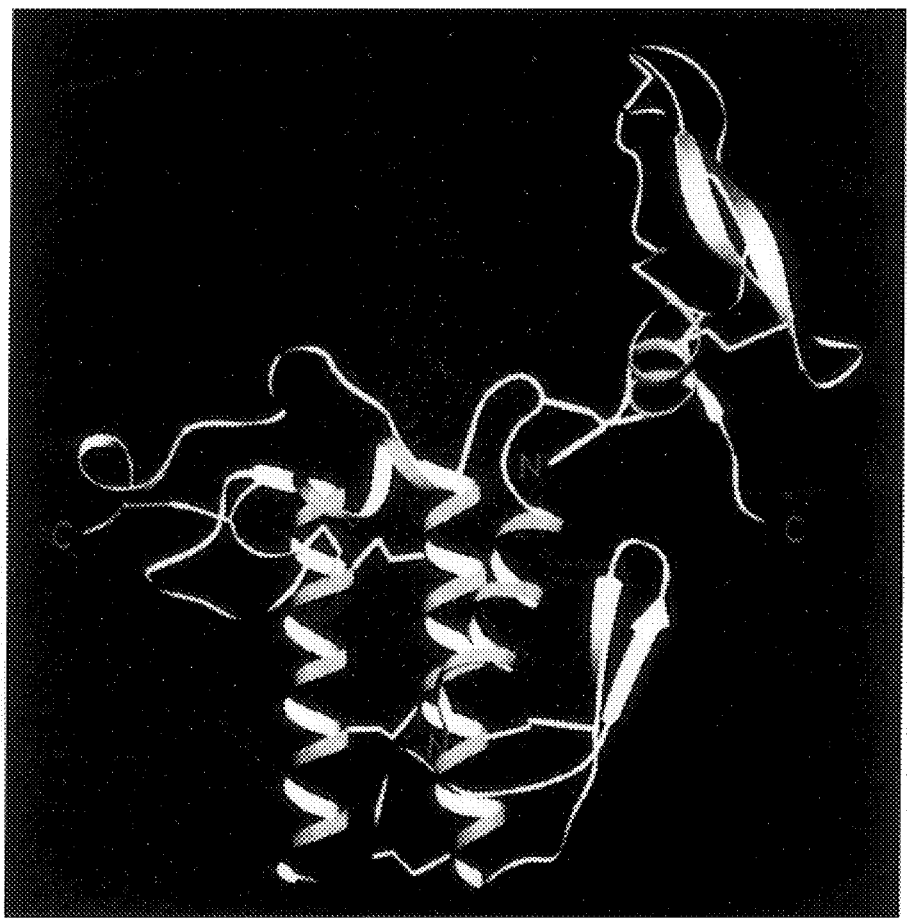
FIGURE 1.2B
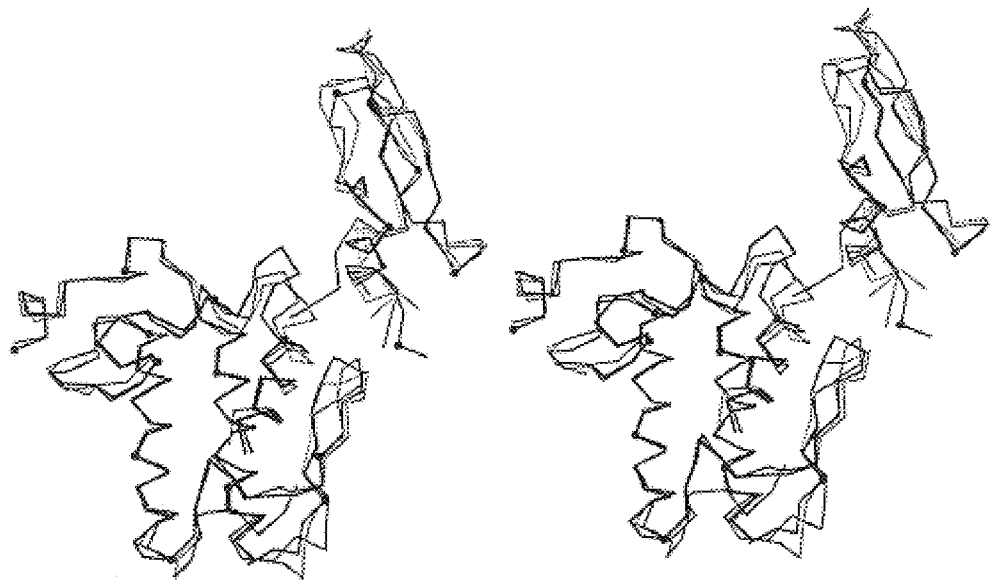

*FIGURE 1.3*

```
               10             20             30             40             50
               |              |              |              |              |
β2-PLA   NLINFMEMIRYT I PCEKTWGEYAD GCYCGAGGSGRPIDALDRC CYVHDNCYGDA EKKHKC
NOTXN    NLVQFSYLIQC ANHGK RPTWHYMD GCYCGAGGSGTPVDELDRC CKIHDDC YKEAGKK G-C
NAJA     NLYQFKNMIQCTVP S RSPWWDFAD GCYCGRGGSGTPVDDLDRC CQVHDNC Y NEAEKI SGC 70             80             90            100           110
               |              |              |              |              |
β2-PLA   NPKTQSYSYKLTKRTIICYGAAGTCARIVCDCDRTAALC FGNSEYIEGHKN IDTARFCQ
NOTXN    FPKMSAYDYYCGENGPYCRNI KKCLRFVCDCDVEAAFC FAKAP N NNANWN DTKKRRCQ
NAJA     WPYFKTYSYECS Q GTLTCK GNN-CAAAVCDCDRLAAIC FAGAPYNDND YN NLKARC 10             20             30             40             50
               |              |              |              |              |
β2-KUN   RKRHPD C DKPPDTKIC Q TVVRAFYYKPSA KR C VQ FRYGG CN GNGNHFKSDH

FIGURE 1.4A
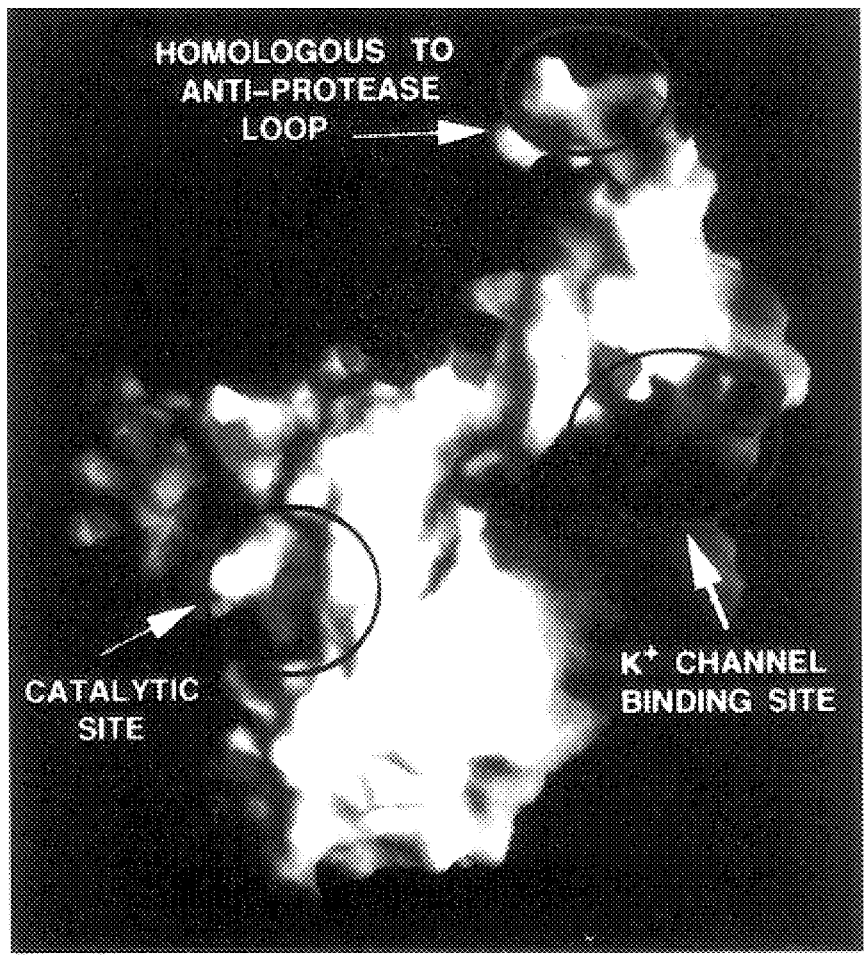
FIGURE 1.4B
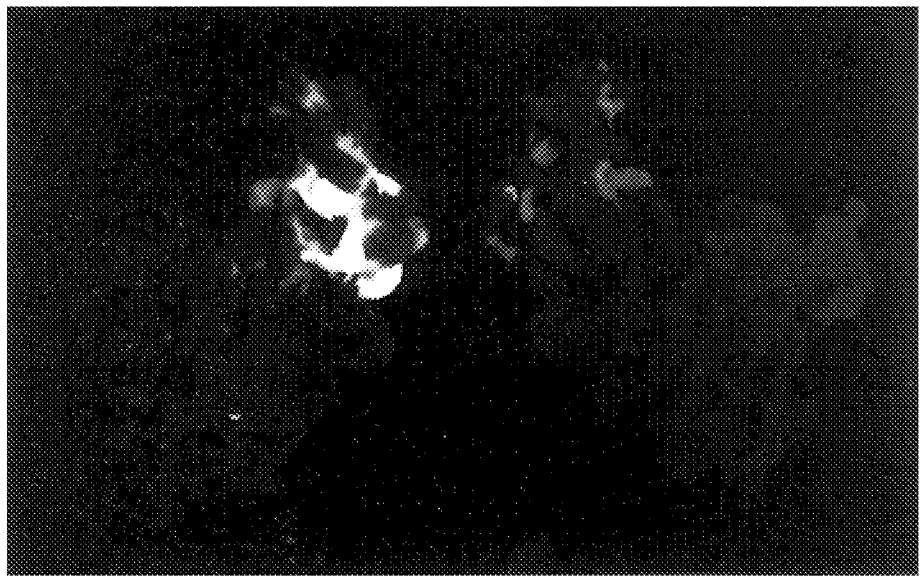

FIGURE 1.5A
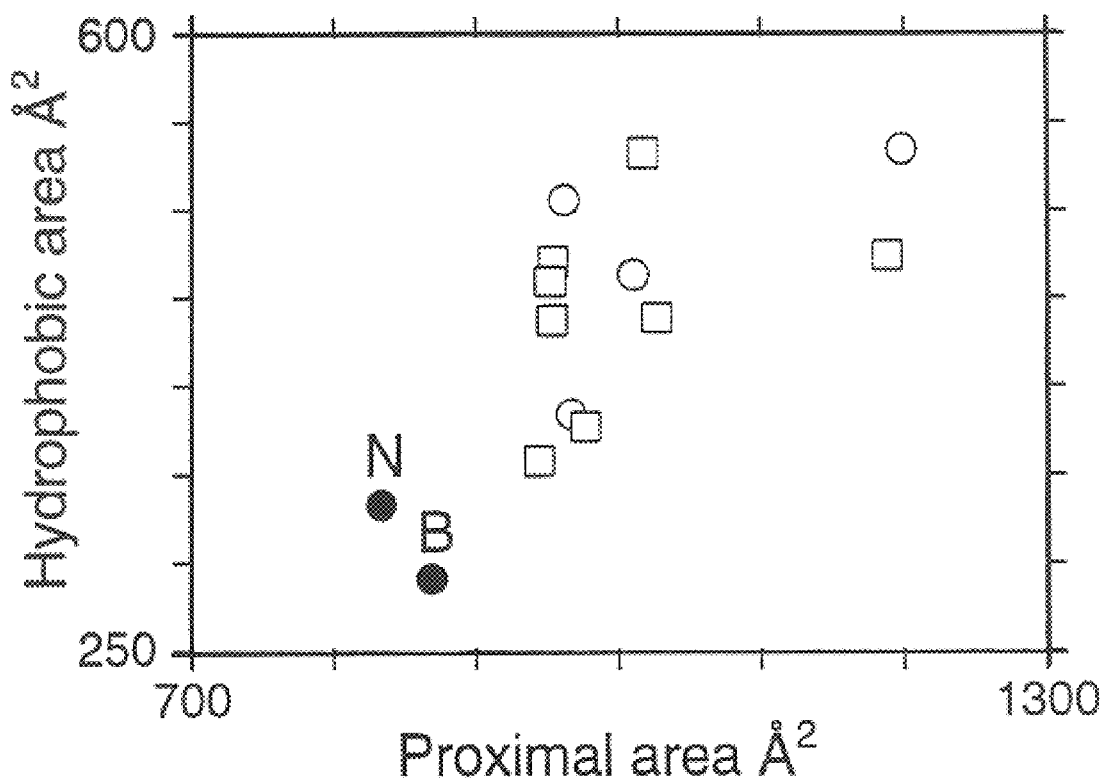
FIGURE 1.5 B
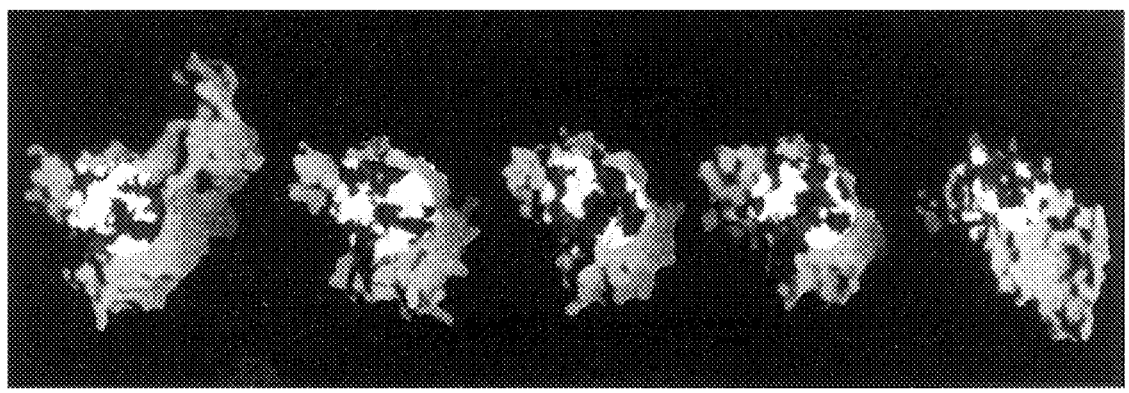

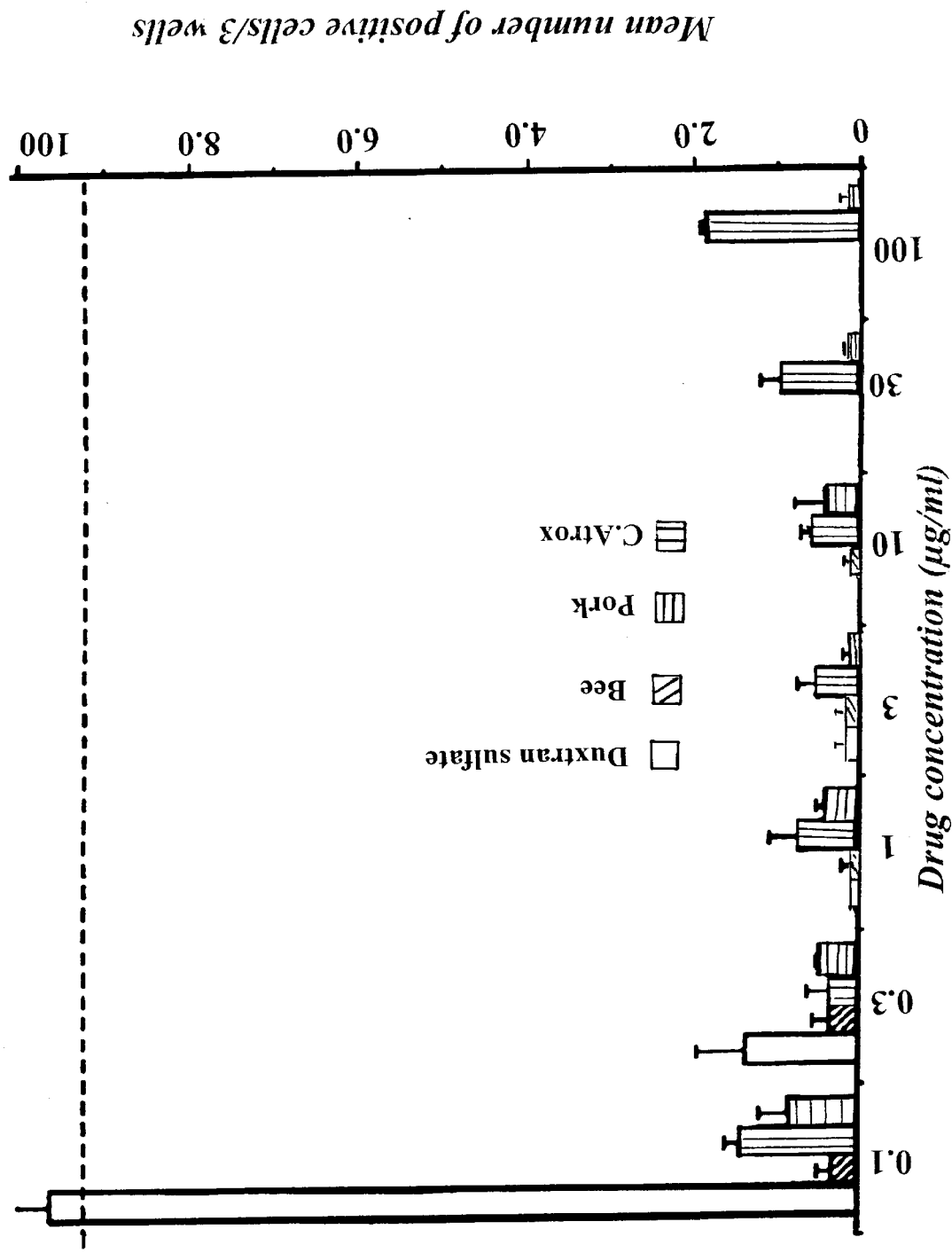
FIGURE 2.1

NON-NATURALLY OCCURRING TARGETED LIPOLYTIC COMPOUNDS AND RELATED COMPOSITIONS AND METHODS

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Virtually all living organisms, including many viruses, use membranes to provide barriers against the external environment. These barriers are essential to maintain the integrity of the organism, with membrane degradation leading to cell death or viral inactivation.

Substances that disrupt membranes serve a diverse number of functions. A few of these include hygiene (soap), the immune system (many lytic pathways including the complement fixation system), and bacterial and animal toxins. These substances have diverse mechanisms; in the case of toxins, they may function by creating pores in the membrane (e.g. colicin), or by enzymatically degrading the lipids which compose the membrane itself (e.g. lipases (reviewed in Wooley and Petersen, 1994) and phospholipases (Scott et al. 1990; reviewed in Vernon and Bell 1992)).

Many lipolytic agents work indiscriminately and thus have limited therapeutic potential. In order to develop a therapeutic reagent, applicants have sought to enhance specificity. One established method for doing so, targeting, uses a molecular guide to direct the reagent specifically to its site of action.

While the idea of targeting cytotoxic agents to pathological cells is an old one (reviewed in FitzGerald and Pastan 1992, Pastan et al. 1992 and in Siegall 1994) the use of reagents which function extracellularly to disrupt membranes has not been attempted. It has several advantages.

First, such reagents would not have to cross the membrane barrier in order to be effective. Such in vivo problems as toxicity, rapid clearance, metabolic inactivation, rapid development of resistance, and low bioavailability remain major hurdles in drug development. One way to avoid or at least to lower the chance that such complications might arise is to use extracellular strategies. Although rapid clearance and development of resistance would still be problematic, extracellular therapeutics would avoid the intricate intracellular machinery, thus lowering toxicity and reducing the rate of metabolic inactivation. Moreover, they would not have to cross into the cytoplasm and thus have higher bioavailability.

Second, such reagents would be effective against the virions of enveloped viruses (such as herpes, influenza, or retroviruses such as HIV), which are resistant to conventional directed toxins. Indeed viruses, which lack cellular biosynthetic repair mechanisms, would be uniquely susceptible to membrane degradation.

As an initial trial, applicants have sought to combine specificity with anti-viral potency through the creation of targeted phospholipases. While applicants have focused on phospholipases as an initial test case, it may be that a different application of the general idea, to specifically target lipolytic agents against pathological cells and enveloped virions, will ultimately prove to be more useful medically.

BRIEF DESCRIPTION OF THE DESCRIPTION

FIG. 1.1 Stereo diagram of electron density produced by combining the multiple isomorphous replacement and the phospholipase molecular replacement phases. Density distributions were calculated with data from 10–2.9 Å, and contoured at 1.0 sigma. The region shown is homologous to the antiprotease loop in the Kunitz subunit and cannot be biased by phase information from the phospholipase model. Shown with it are the final $\beta_2$-bungarotoxin refined model (light green) and a ribbon trace of the backbone and disulfides of BPTI (pink), superimposed as described in FIG. 1.2. Figure made with SETOR (Evans, 1993).

FIG. 1.2 Backbone structure of $\beta_2$-bungarotoxin. (Left) Schematic displaying secondary structural elements. (Right) Stereoplot of the α-carbon atom (Cα) backbone of $\beta_2$-bungarotoxin shown superimposed with toxin (notexin and α-dendrotoxin; dashed line), and non-toxic (*Naja naja atra* phospholipase and BPTI; thin line) homologues of each subunit. Superpositions were made using all Cα that remained within 2.5 Å of each other after least-squares alignment. Outliers are detailed in FIG. 1.3. Balls are drawn every 10 residues for reference. FIG. 1.2*a* was made with SETOR (Evans, 1993), FIG. 1.2*b* with MOLSCRIPT (Kraulis, 1991).

FIG. 1.3 Sequence of $\beta_2$-bungarotoxin aligned with subunit homologs. The sequence of $\beta_2$-bungarotoxin was redetermined from the purified protein. It is shown aligned with toxin and non-toxic homologs respectively of each subunit: phospholipase subunit (notexin and *Naja naja atra* phospholipase) and Kunitz subunit (a-dendrotoxin and BPTI). These sequences have been aligned based on the superposition of their crystal structures (FIG. 1.5). Also shown for the Kunitz subunit are the sequences of two ion channel toxins, calcicludine and mast cell degranulating peptide, although less structural detail is available for them. Yellow, sequence conserved only among Kunitz toxins; cyan, sequence conserved between all Kunitz toxins and BPTI; green, sidechains within 2 Å of the surface as defined by the substrate acyl chains (see FIG. 1.5); ○, catalytic residues in the phospholipase; #, reactive-site Lys or Arg residue of Kunitz serine protease inhibitors; Δ intermolecular half-cystines and residues with more than 25% of their solvent accessible surface buried in the subunit interface; ●, buried amino acid sidechains of the Kunitz subunit of $\beta_2$-bungarotoxin with solvent accessibilities of less than 15%; boxed, residues which differ from $\beta_2$-bungarotoxin by more than 2.5 Å after alignment as detailed in FIG. 1.2.

FIG. 1.4 Molecular surface of $\beta_2$-bungarotoxin. (Top) Electrostatic potential computed with GRASP (Nicholls et al. 1991) at neutral pH. Blue represents positive potential, red negative, and white neutral. The positions of selected features are highlighted. (Bottom) $\beta_2$-bungarotoxin surface colored according to the sequence similarity of the underlying residues. The color scheme is similar to that of FIG. 1.3: conserved only among Kunitz toxins (yellow), conserved between all Kunitz toxins and BPTI (cyan), and unconserved (dark blue). Backbone atoms were considered conserved unless they diverged structurally by more than 2.5 Å as detailed in FIG. 1.3. The yellow patch towards the center of the Kunitz subunit corresponds to Phe 23. Clustered below it are Lys 30 and Arg 54. Opposing views of the toxin were rendered by GRASP.

FIG. 1.5 Chemical and physical properties of the phospholipase surface proximal to the substrate binding region. (Top) Hydrophobic area and proximal area of the surface within 7.5 Å of the substrate acyl chains. Shown are (●) toxic phospholipases, (○) non-toxic phospholipases from structures without substrate, and ([ ]) non-toxic phospholipases from structures of substrate complexes. "N" and "B" label notexin and $\beta_2$-bungarotoxin respectively. (Bottom)

Phospholipase molecular surface colored by the physical properties of the underlying atoms. Green represent hydrophobic, magenta charged, white polar. Portions of the surface that are greater than 7.5 Å from the substrate acyl chains are colored orange. The surfaces depicted with GRASP are (from left to right) $\beta_2$-bungarotoxin, notexin, and the phospholipases from cobra (*Naja naja atra* class I), rattlesnake (*Crotalus atrox* class II), and honeybee (*Apis mellifera* insect). Figure made with GRASP (Nicholls et al., 1991).

FIG. 2.1 Phospholipase $A_2$ inactivation of HIV. HIV-1 virions were incubated with various inactivating reagents for 4 hours at 37° C. Hela cells (CD4$^+$ containing an LTR-HIV dependent promoter-LacZ fusion) were subsequently added and the mixture incubated for 2 hours at 37° C. Cells were centrifuged, trypsinized, transferred to 96-well $\mu$-titre plates, and incubated for an additional 48 hours at 37° C., and then fixed and stained with X-Gal. Blue cells, indicating the presence of an HIV-Tat activated LacZ gene, were counted. Shown are Dextran sulfate (a previously identified potent in vitro HIV inactivating reagent), Bee (an evolutionarily divergent phospholipase $A_2$ from bee venom), pork (a monomeric digestive phospholipase $A_2$ from porcine pancreas), and C. Atrox (a dimeric venom phospholipase $A_2$ from the snake, *Crotalus atrox*). Various concentrations of these reagents and their inactivating effect on HIV are shown. The dotted line corresponds to the number of positive cells in the control where no inactivating reagent was added. The lowest concentration, 0.1 $\mu$g/ml, corresponds to a concentration of roughly 7 nM for the phospholipase.

DETAILED DESCRIPTION OF THE INVENTION

This invention provides a non-naturally occurring targeted lipolytic compound comprising a lipolytic agent linked to a targeting agent.

As used herein, the term "non-naturally occurring" means the targeted lipolytic compound does not exist in nature. As used here, a lipolytic agent is capable of causing membrane lysis. A targeting agent can preferentially bind to a specified cell, virus, or molecule.

In an embodiment, the lipolytic agent of the targeted lipolytic compound is a lipase. In a further embodiment, the lipase is a phospholipase. In a still further embodiment, the phospholipase is a phospholipase A2. In a further embodiment, this phospholipase A2 is a phospholipase subunit of $\beta$-bungarotoxin.

The lipolytic agent and the targeting agent are linked physically in such a manner as to not adversely affect the individual activity of each subunit. Such linkage may be direct or indirect. As used here, direct linkage refers to any linkage between lipolytic agent and targeting agent that does not require a linkage agent. Indirect linkage refers to any linkage which does require a linkage agent. Examples of indirect linkages include but are not restricted to: 1) a crosslinking reagent, if the lipolytic agent and targeting agent are separate molecules; or 2) a peptide linking region, if the compound is produced by genetic manipulation. Furthermore, such linkage may result from covalent bonding, non-covalent interactions, or a combination of the two. In an embodiment, the lipolytic agent of the non-naturally occurring targeted lipolytic agent is covalently linked to the targeting subunit. In a separate embodiment, the lipolytic agent of the non-naturally occurring targeted lipolytic compound is linked to the targeting subunit by non-covalent interactions.

This invention provides the above-described targeted lipolytic compound wherein the targeting agent preferentially recognizes a virus.

This invention provides the above-described targeted lipolytic compound wherein the targeting agent preferentially recognizes a subpopulation of cells.

This invention further provides the above-described targeted lipolytic compound wherein the targeting agent preferentially recognizes a pathological cell.

This invention provides the above-described non-naturally occurring targeted lipolytic compound wherein the targeting subunit is a protein. In an embodiment, the protein is a monoclonal antibody. In another embodiment, the protein is an antibody or a portion of an antibody with the ability to bind antigen.

In a separate embodiment, the targeting agent comprises a carbohydrate molecule. In another embodiment, the targeting agent is a drug.

This invention also provides the above-described non-naturally occurring targeted lipolytic compound wherein the targeting agent is a protein capable of specifically recognizing an epitope on the surface of a virus. In an embodiment, the virus is an envelope virus. In a further embodiment, the virus is selected from a group consisting essentially of herpesviruses, poxviruses, arboviruses, myxoviruses, orthomyxoviruses, paramyxovirus, leukoviruses, hepatitis viruses and retroviruses.

In a further embodiment, the targeting agent is preferentially recognized by human immunodeficiency virus.

In an embodiment, the targeting subunit is a Soluble CD4 (sCD4) molecule. In a further embodiment of the above-described non-naturally occurring targeted agent, the targeting subunit is sCD4 and the lipolytic is a phospholipase.

This invention further provides the above-described targeted lipolytic compound which targets to a pathological cell, wherein the pathological cell is a tumor cell. In an embodiment, the pathological cell is a virus infected cell. In another embodiment, the pathological cell is a genetically aberrant cell.

This invention further provides a therapeutic composition comprising the above-described non-naturally occurring targeted agent and a pharmaceutically acceptable carrier.

For the purposes of this invention "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

This invention also provides a method of inactivating virions which comprises contacting the virion with the above-described targeted lipolytic compounds at an effective concentration permitting killing of the virions, thereby inactivating the virions.

This invention also provides a method of selectively eliminating a subpopulation of cells in a sample which comprises contacting the sample with the above-described targeted lipolytic compound, wherein the targeting agent preferentially recognizes the subpopulation of cells for an appropriate time permitting the lipolysis of cells by the lipolytic agent, thereby eliminating the subpopulation of cells in the sample.

This invention also provides a method of killing pathological cells which comprises contacting the pathological cells with the above-described targeted lipolytic compound at an effective concentration permitting killing of cells, thereby killing the pathological cells. In an embodiment, the cells are tumor cells. In another embodiment, the cells are virus infected cells. In a further embodiment, the cells are genetically aberrant cells.

This invention will be better understood from the Experimental Details which follow. However, one skilled in the art will readily appreciate that the specific methods and results discussed are merely illustrative of the invention as described more fully in the claims which follow thereafter.

SUMMARY OF EXPERIMENTS

Applicants performed three experiments which are summarized here. Experimental details follow after the summary.

Experiment 1

X-ray crystallographic analysis of the neurotoxin, β-bungarotoxin, from the venom of the snake *Bungarus multicinctus:* elucidation of functional mechanism and discussion of therapeutic adaptation.

β-Bungarotoxin consists of two subunits, a phospholipase subunit which functions extracellularly to degrade lipid membranes, and a targeting subunit, which serves to guide the phospholipase to its site of action at the presynaptic membrane, potentiating its toxic degradative ability. From detailed structural analysis of this naturally occurring, evolutionarily perfected toxin, applicants elucidated its mechanism of action. This mechanism may have beneficial application in other contexts, and applicants discuss the creation of extracellularly targeted therapeutics.

Experiment 2

Demonstration of lipolytic potency, extension to enveloped virions.

Applicants explored the use of lipolytic agents, some of which function extracellularly and may be adapted to therapeutic application. In one particular example, applicants focused on the neutralizing abilities of lipolytic phospholipases. While the sensitivity of most cells to phospholipase degradation is well-documented, applicants sought to extend the therapeutic range of applicability to enveloped viruses. Applicants tested the ability of extracellular phospholipases to neutralize enveloped virions, which are virtually inert biochemically and resistant to activation by many drugs. Applicants demonstrated that the virions of the enveloped retrovirus HIV were extremely susceptible to phospholipase degradation.

Experiment 3

Therapeutic conjugates: creation and application of a non-naturally occurring targeted lipolytic compound.

When separated from its natural targeting subunit (which directs it to the presynaptic membrane), the β-bungarotoxin phospholipase is not toxic. Applicants succeeded in separating and purifying the β-bungarotoxin phospholipase subunit, while maintaining its phospholipase activity. Chemical conjugates were created consisting of the β-bungarotoxin phospholipase covalently attached to human CD4, the receptor for HIV. Applicants demonstrated that these conjugates were 10-times more effective at inhibiting HIV replication than either dextran sulfate or pentane sulfate, both of which are accepted as potent standards for in vitro inhibition of HIV.

EXPERIMENTAL DETAILS

Experiment 1

X-ray crystallographic analysis of the neurotoxin, β-bungarotoxin, from the venom of the snake *Bungarus multicinctus:* elucidation of functional mechanism and discussion of therapeutic adaptation.

Experiment 1 Abstract

The presynaptic neurotoxin β-bungarotoxin consists of an enzymatic phospholipase subunit linked by a disulfide to a targeting subunit, which is a member of the Kunitz protease-inhibitor superfamily and binds voltage sensitive $K^+$ channels. The crystal structure was solved and refined at 2.45 Å resolution. Analysis of the phospholipase subunit reveals a partially occluded substrate binding surface and reduced hydrophobicity, functional adaptations which make this phospholipase uniquely suited to targeting. Not only is the targeting activity segregated to a separate subunit, but the calcium dependent nature of the phospholipase confines lipolytic hydrolysis to the extracellular surface, thus avoiding intracellular machinery and reducing toxicity and the rate of metabolic inactivation. Most pathological cells should be sensitive to lipolytic degradation. Moreover, by recoupling the phospholipase to a viral receptor moiety, such phospholipase therapy may also work on enveloped virions; the very biochemical inertness which makes virions resistant to conventional directed toxins should make them particularly sensitive to phospholipase degradation. Insight into the mechanism of β-bungarotoxin may thus lead to the development of therapeutic strategies against not only pathological cells but also enveloped viruses.

Introduction of Experiment 1

β-bungarotoxin is a heterodimeric neurotoxin from the venom of the snake *Bungarus multicinctus* (Chang & Lee, 1963 and Abe et al., 1977). It contains a lipolytic phospholipase $A_2$ subunit, which closely resembles an extensively characterized family of extracellular phospholipases found in venom, pancreatic secretions, and inflammatory exudates (Scott et al., 1990, reviewed in Dennis, 1994). It also contains a second subunit, which is a member of the Kunitz (Kunin or pancreatic trypsin type) protease-inhibitor superfamily, although β-bungarotoxin demonstrates no protease inhibitor capacity (Kondo et al., 1982a, reviewed in Laskowski & Kato, 1980 and Bode & Huber, 1992). This subunit serves to guide the toxin to its site of action on the presynaptic membrane by virtue of a high affinity interaction (nanomolar $K_d$) with a specific subclass of voltage sensitive $K^+$ channels (Rehm & Betz, 1984; Petersen et al., 1986 and Rehm & Tempel, 1991). With more than a dozen structures known at atomic resolution for representative members of each family, analysis of these subunits in the unusual context of a disulfide-linked neurotoxin provides a unique opportunity to understand the essential modifications needed for targeted toxicity. Although the interaction of the Kunitz module with proteases has been extensively characterized, its interaction with ion channels is not well understood; knowledge of this interaction might aid in understanding the regulation of ion channels. Moreover, as potent and specific effectors of the nervous system, these Kunitz toxins have been the focus of drug design efforts (Smith et al., 1993, reviewed in Hasrvey et al. 1994). In β-bungarotoxin, the Kunitz subunit must specifically recognize the ion-channel receptor, while (unlike targeted cytotoxins) simultaneously permitting phospholipase enzymatic hydrolysis. Because of its role in guiding the toxin, applicants have termed the Kunitz subunit the "targeting subunit" and applicants refer to the mechanism of β-bungarotoxin as "targeted phospholipase" action.

A number of venom phospholipases are toxic and, although they appear to share similar biochemical properties (Radvanyi et al., 1987), they vary mechanistically. For example, the neurotoxin, crotoxin, is composed of a standard phospholipase and an inhibitory chaperone, which blocks the phospholipase active site until triggering by a presynaptic receptor causes it to dissociate (Delot & Bon, 1993). In contrast, the monomeric phospholipases from *Oxyuranus scutellatus* are unchaperoned, yet they specifically target skeletal muscle (Lambeau et al., 1990). A review of the primary structures of all known phospholipase toxins reveals that only one, β-bungarotoxin, consists of a simple bipartite structure and mechanism of action in which targeting and phospholipase activity are separated into non-homologous subunits (Chang, 1985).

As with immunotoxins (reviewed in FitzGerald & Pastan, 1989 and Press, 1991), the bipartite structure of β-bungarotoxin may be of use in the design of directed toxins of therapeutic value. β-Bungarotoxin has several therapeutic advantages. Unlike other highly toxic phospholipases, it is extremely specific in its effects; it does not have either direct or indirect hemolytic activities (Ho et al., 1986). Moreover, at concentrations of only 1–2 nM, it specifically suppresses cultured neuronal cell growth while maintaining a high population of viable photoreceptor cells (Politi & Adler, 1986).

When purified from snake venom, β-bungarotoxin is found to consist of a number of different isoforms, six of which have been characterized by sequencing (Kondo et al., 1982a and 1982b). Applicants report here the structure of the $\beta_2$-isoform. Sequence and structure analyses reveal surprisingly novel modes of interaction between this toxin and ion-channels and lipid membranes. Insight into these interactions may be useful in other contexts: applicants discuss the relevance of toxin binding to ion-channel regulation and the therapeutic potential of a redirected phospholipase against enveloped viruses like HIV.

Experimental Results and Discussion for Experiment 1

Overall Structure

The structure of $\beta_2$-bungarotoxin was solved at 2.45 Å resolution by a combination of molecular replacement and MIR phasing techniques and refined to an R-value of 19.3% (Table 1.1, FIG. 1.1). The structure of $\beta_2$-bungarotoxin is shown in FIG. 2*a*. Although each subunit is relatively globular, their joining produces a relatively extended molecule of mainchain dimensions ~60×40×20 Å.

TABLE 1.1

| parameter | Native 1 | Native 2 | $BaCl_2$ | p-CMBS# | $K_2PtBr_6$ |
|---|---|---|---|---|---|
| Structure determination | | | | | |
| Crystal stabilization | | | | | |
| NaCl (M) | 3.5 | 4.75 | 3.5 | 4.75 | 4.75 |
| Data collection statistics | | | | | |
| Resolution (Å) | 10–2.45 | 10–3.3 | 7–2.9 | 10–3.3 | 10–6.0 |
| Observations | 30515 | 17126 | 25777 | 17856 | 3400 |
| Unique | 9372 | 3758 | 5125 | 3738 | 551 |
| With Bijovets | — | — | 4760 | 3528 | 538 |
| Completeness (%) | 96.4 | 93.1 | 91.7 | 92.7 | 92.6 |
| With Bijovets | — | — | 85.2 | 87.5 | 90.4 |
| $R_{sym}$* (%) | 6.9 | 7.2 | 6.9 | 7.6 | 4.9 |
| Phasing statistics | | | | | |
| Mean isomorphous difference † | | | 0.175 | 0.256 | 0.132 |
| Cullis R factor‡ | | | 0.550 | 0.571 | 0.577 |
| Phasing power§: | | | | | |
| isomorphous | | | 1.9 | 1.8 | 2.1 |
| anomalous | | | 0.8 | 0.6 | 0.4 |

*$R_{sym} = \Sigma|Iobs - Iavg| / \Sigma Iavg$.
†The mean isomorphous difference is $\Sigma |F_{PH}-F_P|/\Sigma F_P$, where $F_{PH}$ and $F_P$ are the derivative and native structure factor amplitudes, respectively.
‡The Cullis R factor is $\Sigma |F_H(obs) - F_H(calc)|/\Sigma F_H(obs)$, where $F_H$ is the heavy-atom structure factor amplitude.
§Phasing power is the mean amplitude of the heavy atom structure factors, $F_H$, divided by E, the root-mean-square lack of closure error.
para-chloromercuribenzene sulphate.

As expected from sequence analysis (Kondo et al., 1982b), the structure of the phospholipase subunit (120 residues and 6 disulfide bonds) closely resembles other members of a large homologous family of phospholipases $A_2$ (Dennis, 1994). The three helices which make up its core as well as the calcium binding loop superimpose well with the non-toxic Class I phospholipase from *Naja naja atra* (Scott et al., 1990) (rms of 0.826 Å for 107 Cα), and the toxic phospholipase notexin (Westerlund et al., 1992) (rms of 0.908 Å for 108 Cα) (FIG. 1.2*b*). Differences are seen mainly in the regions which interact with the Kunitz subunit (residues 13–16 and 74–76), close to the substrate binding loop (residues 63–65), and at the base of the beta-wing (residues 81–84).

The Kunitz subunit with 61 residues and 3 disulfides bonds also closely resembles other Kunitz superfamily members; it superimposes well with the classical protease inhibitor, bovine pancreatic trypsin inhibitor (BPTI) (Huber et al., 1970 and Deisenhofer & Steigemann, 1975) (rms of 0.955 Å for 48 Cα) and with the Kunitz toxin, a-dendrotoxin (Skarzynski, 1992) (rms of 0.837 Å for 49 Cα) (FIG. 1.2*b*). Deviations are concentrated in the amino terminus (which in $\beta_2$-bungarotoxin interacts with the phospholipase subunit) and in the region homologous to the antiprotease loop (which in conventional Kunitz protease inhibitors is involved in protease binding).

Subunit Interface

A novel Kunitz interaction observed in $\beta_2$-bungarotoxin involves the intersubunit disulfide bridge at the C-terminal α-helix, namely, Cys 55 of the Kunitz subunit to Cys 15 of the phospholipase subunit. The subunit interface buries 1247 $Å^2$, with 153 $Å^2$ contributed by the half-cystine residues. Although hydrophobic contacts with Tyr are observed, charged residues predominate in the interface (FIG. 1.3). A $\beta_2$-bungarotoxin-like intermolecular disulfide bridge may also be observed in the C-terminal domain of the morphogen NOGGIN, a dorsalization factor involved in head formation in Xenopus oocytess (Smith & Harland, 1992). While the NOGGIN sequence conserves the seven cysteine residues of the β-bungarotoxin Kunitz domain (McDonald & Kwong, 1993), the NOGGIN disulfide bond bridges a homodimer, and, apart from the conserved cysteine, none of the residues that stabilize the β-bungarotoxin interface are retained.

Targeting Selectivity and Phospholipase Subunit

The remarkable capacity of the toxin to avoid non-specific binding and exclusively hydrolyze the presynaptic membrane is central to its neurotoxic action. Because its substrate, phospholipid, is continually present in abundance in non-target membranes, β-bungarotoxin faces special targeting problems. Even though the phospholipase subunit of the toxin has almost 60% sequence identity with other venom and pancreatic phospholipases, its interactions with membranes are markedly different (Radvanyi et al., 1987). Non-toxic phospholipases bind membranes (and micelles) in a non-specific promiscuous manner; β-bungarotoxin binds poorly to zwitterionic and non-ionic micelles ($K_d>>60$ mM). It exhibits a much greater degree of selectivity for anionic surfaces than other phospholipases (Radvanyi et al., 1987). Applicants analyzed the phospholipase subunit for clues to the functional adaptations required for targeted neurotoxicity.

Structurally, the substrate binding loop (residues 60–65), which influences membrane binding and is one of the most variable features of the phospholipase family (Kuipers et al., 1989), was found to be closely related to that of the non-toxic phospholipase from *Naja naja atra* (FIG. 1.2).

Electrostatically, the substrate binding region was found to be negatively charged, the same as its preferential binding surface (FIG. 1.4). While the overall charge of the toxin (+8 at neutral pH, most of which resides in the Kunitz subunit) may account for a non-specific affinity for anionic surfaces, other phospholipases have substantial net positive charges and are not neurotoxic (e.g., the eastern cottonmouth phospholipase with +9 charges (Maraganore & Heinrikson, 1986)). These observations would tend to rule out conjectures explaining the toxic activity of β-bungarotoxin in terms of a structural binding feature or a specific electrostatic interaction.

With respect to the chemical and physical properties of the surface proximal to the substrate binding site, however, α-bungarotoxin clearly segregates from non-toxic phospholipases, showing both reduced hydrophobicity and reduced proximal surface area (FIG. 1.5). These two properties may be related through an association between surface curvature and hydrophobicity (Nicholls et al., 1991) and account for the weak non-ionic micelle binding of the toxin. They may also reflect a functional adaptation for neurotoxicity which reduces the non-specific affinity of the toxin for membranes and thereby enhances targeting specificity. Indeed, the other neurotoxic phospholipase included in the analysis, the monomeric notexin (Westerlund et al., 1992), segregates in the same fashion as β-bungarotoxin (FIG. 1.5).

Crystal structures of several phospholipase $A_2$-substrate complexes demonstrate that this class of phospholipases bind substrate in a conserved manner (Scott et al., 1990). Modeling of the phospholipid substrate into the active site of β-bungarotoxin leads to steric clashes with Trp 19, which appears to partially occlude the hydrophobic substrate binding site. Torsional rotation of Trp 19 out of the active site—to the most favorable, sterically allowed, rotamer conformation (Ponder & Richards, 1987), similar to that seen in the structure of the substrate complex of *Naja naja atra* phospholipase (Scott et al., 1990)—would position its indole ring within the membrane. Such a conformation would increase both the hydrophobic and proximal surface area of the toxin by approximately 100 Å$^2$, aligning it with non-toxic phospholipases. Thus, while surface properties are a cumulative reflection of all of the exposed residues, Trp 19 may play a central role, in occluding the substrate binding site during diffusion to the presynaptic membrane, and once at the membrane, acting as a hydrophobic anchor to facilitate tighter binding. Other phospholipases may also occlude their substrate binding sites as a general mechanism for enhancing diffusion; Trp 19 is not unique to β-bungarotoxin and oligomerically shielded substrate binding sites have been observed in the crystal structures of several venom phospholipases (Brunie et al., 1985 and Fremont et al., 1993).

Therapeutic Adaptation of β-bungarotoxin

The molecular mechanisms revealed here, by which β-bungarotoxin avoids non-specific membrane interactions, coupled with the segregation of targeting activity to a separate subunit (which may be removed by selective reduction) make the β-bungarotoxin phospholipase uniquely suited to therapeutic adaptation. As with targeted toxin therapy, it should be possible to redirect the β-bungarotoxin phospholipase by switching its targeting subunit from the Kunitz module to, for example, a pathogen receptor or tumor specific antibody. Such a redirected phospholipase would have several advantages over the typical targeted cytotoxins (e.g., ricin, exotoxin A, and cholera toxin) used in toxin therapy. In order to function, these must be internalized and translocated to the cytoplasm, a relatively inefficient process; several thousand toxin molecules may be stranded at the cell surface before one reaches the cytoplasm (FitzGerald & Pastan, 1989 and Hudson & Grillo, 1991). In contrast, the β-bungarotoxin phospholipase degrades membranes extracellularly. Such phospholipase therapy may also work on the virions of enveloped viruses (such as herpes, influenza, or retroviruses like HIV), which are resistant to conventional directed toxins. Indeed viruses, which lack cellular biosynthetic repair mechanisms, would be uniquely susceptible to this type of membrane degradation.

Materials and Methods for Experiment 1

Protein purification and crystallization $β_2$-Bungarotoxin was purified from the venom of *Bungarus multicinctus* (Miami Serpentarium) as previously described (Kondo et al., 1982a), except that an additional Mono-S (Pharmacia) chromatographic step at pH 8.8 was included. Crystals (space group $P4_322$ with cell dimensions: a=52.6 Å, c=177.5 Å, one molecule per asymmetric unit) were grown from hanging droplets composed of 7 μl of 10 mg/ml protein, 0.5 mM EDTA, 0.01% NaN$_3$, 1.4 M NaCl, equilibrated over 1.0 ml reservoirs of 3.3 M NaCl, 50 mM Tris/HCl pH 8.5 at 20° C.

Data Collection and Molecular Replacement

Data were collected on a Xuong-Hamlin area detector using CuK$_α$ radiation from a Rigaku rotating anode. Molecular replacement phasing as implemented in XPLOR (Brunger, 1992a) was attempted using a model of bovine phospholipase $A_2$ (Dijkstra et al., 1981) that included backbone atoms and conserved amino acid sidechains. Using data with Bragg spacings between 10–4 Å, Patterson correlation refinement (Brunger, 1990) resulted in a dominant rotation peak (0.079 correlation, 20% higher than the next highest peak) which produced a clear translation solution (0.286 correlation in $P4_322$ against 0.190 in $P4_122$). After rigid body refinement (correlation 0.329), the contribution of each amino acid to the correlation was checked by successive deletions, and the search model pruned accordingly. This improved the correlation to 0.419. visual inspection of electron density maps produced with these phospholipase model phases failed to give an indication of the orientation of the Kunitz subunit. Molecular replacement searches with numerous BPTI models also failed.

Multiple Isomorphous Replacement, Model Building, and Refinement

A 20 mM BaCl$_2$ derivative was prepared by co-crystallization. Other derivatives (5 mM, 24 hr equilibration) were screened using crystals stabilized in 4.75 M NaCl, 50 mM Tris pH 8.5. Derivative atom positions were determined from difference Fourier by using the phospholipase model phases. Native and derivatives with different stabilization conditions were kept separate through heavy atom refinement and phase calculations (REFINE and PHASE (Collaborative Computational Project, No. 4, 1994)), until protein ABCD coefficients could be combined (Hendrickson & Lattman, 1970). Each derivative contained a single site. Anomalous differences were included in all heavy atom calculations. A model for the phospholipase subunit was built into the MIR electron density. Phase combination between this model and the experimental MIR allowed the entire β-bungarotoxin model to be built. Subsequent refinement (XPLOR) reduced the R-value to 19.3% (5–2.45 Å, all data greater than 2 sigma, with 10% of the data removed for free R-value calculation (Brunger, 1992b)) with tightly restrained individual isotropic B-values, and RMS deviations of bond of 0.011 Å and angles 1.6 degrees. The present model contains 1523 non-hydrogen atoms including 82 waters and 1 Na$^+$ ion modeled into the calcium binding loop (the crystallization contained over 3 M Na$^+$ and EDTA which chelated all free calcium). The free R-value (Brunger, 1992b) is 28.0%.

β$_2$-Bungarotoxin Protein Sequencing

Kunitz subunit: It was clear from the initial electron density maps that the published sequence of the Kunitz subunit of β$_2$-bungarotoxin (Kondo et al., 1982a) was incorrect. Applicants resequenced the Kunitz subunit using material purified for crystallization. The disulfide bonds of β$_2$-bungarotoxin were reduced and alkylated with iodoacetamide. After purification on reverse phase HPLC, the reduced and alkylated Kunitz subunit was proteolyzed with endoproteinase Lys-C. Resulting peptides were separated by reverse phase HPLC and sequenced on an Applied Biosystems 470A sequencer. The revised sequence is shown in FIG. 1.3.

Phospholipase subunit: The five reported β-bungarotoxin phospholipase sequences, three from protein sequencing (Kondo et al., 1982b) and two from cDNA nucleotide sequencing (Danse et al., 1990a and Danse et al., 1990b), show greater than 90% identity. At each phospholipase amino acid where isoform differences had been reported, applicants examined the experimental electron density and on the basis of this, made five substitutions to the reported β$_2$-bungarotoxin sequence (Kondo et al., 1982b): S66Q, Q67S, G87A, Q103N, D105E. All of these substitutions conform to the reported nucleotide sequences.

Analysis of Phospholipase Surface

The physical and chemical properties of surfaces of 14 phospholipase crystal structures were analyzed with GRASP (Nicholls et al., 1991). These include toxins (β$_2$-bungarotoxin, notexin (Westerlund et al., 1992)), phospholipases without substrate (Protein data bank accession codes 1BP2, 1BPQ, 1P2P, 1POA, 1POD, 1PPA, 1PP2, 1PSH), and substrate complexes (1POB, 1POC, 1POE, 5P2P). All phospholipases except for bee phospholipase (see below) were oriented to a common frame by superimposition onto β$_2$-bungarotoxin. Superpositions used the mainchain atoms of the three invariant helices which define the core. The rms deviations ranged between 0.4 and 0.6 Å for the superimposed helices. The collection of substrate complexes aligned in this manner, showed similar substrate orientations. The solvent accessible surface (as defined by a 1.4 Å probe) of each phospholipase, 7.5 Å from the hydrophobic acyl chains of this collection of superimposed substrates, was analyzed with respect to the chemical character of the underlying atoms. Sidechain atoms in Asp, Glu, Lys, and Arg residues were considered charged, carbon atoms in Val, Ile, Leu, Met, Trp, and Tyr residues, hydrophobic, and all other atoms including the backbone, polar. Quantitative measurements were made by calculating the surface area covering atoms of each chemical characteristic. (Because of its structural divergence, bee phospholipase could not be oriented by its protein structure. The bee phospholipase substrate complex (1POC) was oriented by superimposing its substrate onto the substrate of the *Naja naja atra* complex (1POB). The RMS of superposition was 0.89 Å for the 24 atoms that remained within 2 Å of each other after least squares alignment. The 7.5 Å radius surface analysis of 1POC was based solely on its own substrate. Regardless, the 1POC hydrophobicity and surface area were indistinguishable from other non-toxic phospholipases).

Experiment 2

Demonstration of Lipolytic Potency: Extension to Enveloped Virions

Lipolytic Phospholipases A2

Phospholipases A2 hydrolyze the sn-2 ester of phospholipids (Scott et al. 1990; reviewed in Vernon and Bell 1992). These extracellular enzymes makeup a large well-characterized family of proteins that preferentially hydrolyze aggregated phospholipids, for example in micelles or membranes. They are found in large amounts in digestive juices as well as in the venom from many snakes and insects.

Since phospholipids are the primary constituent of membranes, phospholipase lipolytic degradation may result in cell lysis, and most eukaryotic cells are susceptible to such degradation. In multicellular organisms, however, such action is usually not very toxic. Phospholipases bind membranes indiscriminately; this restricts diffusion and damage is confined locally.

Some toxic phospholipases have evolved methods of enhancing diffusion and of specifically targeting a select subset of cells (reviewed in Chang 1985). In this they resemble targeted cytotoxins (reviewed in FitzGerald and Pastan 1989). In the case of β-bungarotoxin (see Introduction to experiment 1), such naturally occurring specific targeting has been used in cell culture to select against a particular subset of cells (Politi and Adler 1986).

The use of phospholipases should be widely applicable. Many living things have membranes. Some of these are not even cellular, for example, the virions of enveloped viruses; nonetheless, phospholipase degradation should be effective at neutralizing these as well.

Phospholipase Inactivation of Enveloped Virions

Many enveloped viruses are capable of causing disease in humans. Among them are Arboviruses (yellow fever), Herpesviruses (oral and genital sores), Orthomyxoviruses (the common flu), Paramyxoviruses (measles and mumps), Poxviruses (smallpox), and Retroviruses (AIDS). Although they remain a continuing scourge, very few therapeutic strategies other than vaccination have been developed that combat them effectively.

Viruses are parasitic. Their virions are virtually inert biochemically, without biosynthetic processes with which to target or endocytosis by which drugs may gain access. Enveloped virions are further protected by lipid membranes and are resistant to most conventional treatments. Nevertheless, applicants sought to exploit this very inertness by using phospholipase hydrolysis as a therapeutic tool. Virions, applicants reasoned, lack biosynthetic repair mechanisms and thus would be uniquely susceptible to this type of membrane degradation.

Virus membranes are also intrinsic components in the virus entry mechanism: virus-cell membrane fusion leads to internalization of the virus core into the cell, initiating the infectious cycle. Thus elimination of the viral lipid envelope prevents virus entry and infection.

As an initial test, applicants assayed the ability of phospholipases to inactivate the enveloped virions of HIV (FIG. 2.1). To ensure that the viral inactivation was a result of phospholipase hydrolysis, and not an unforeseen side effect, applicants tested three widely divergent phospholipases. Dextran sulfate was used as a standard by which to judge viral inactivation potency. Dextran sulfate has previously been established to be an efficient inactivator of HIV virions in vitro, although it appears to function non-specifically and is thus not a viable therapeutic agent (Abrams et al. 1989).

The initial test was a success. The phospholipases were found to be all extremely potent, inactivating HIV more effectively than dextran sulfate. No effect was found on cell viability at concentrations 1000 times higher than that needed for virion inactivation.

EXPERIMENT 3

Therapeutic Conjugates: Creation and Application of a Non-naturally Occurring targeted Lipolytic Compound The therapeutic use of targeted toxins has been investigated extensively over the past 20 years (reviewed in Pastan et al. 1992 and in Siegall 1994). But the plant and bacterial toxins used thus far have consisted almost exclusively of inhibitors of protein synthesis. In order to function, these must be internalized and translocated to the cytoplasm, an inefficient process—several thousand toxin molecules may be stranded at the cell surface before one reaches the cytoplasm (Hudson and Grillo 1991; reviewed in FitzGerald and Pastan 1989). In contrast, phospholipases do not need to be internalized. They may function extracellularly. Moreover, their targets are not necessarily cellular, extending their potential therapeutic range to include not only pathological cells, but also enveloped viruses. In the specific case of HIV, it should be possible to conjugate the CD4 protein to the β-bungarotoxin phospholipase. Such a conjugate would combine CD4-directed specificity, with phospholipase derived potency. Whether such conjugates prove useful therapeutically can only be determined experimentally. The general concept of targeting lipolytic agents against virions may serve as a universal therapeutic strategy against pathological enveloped viruses.

Preparation of β-bungarotoxin Phospholipase

β-bungarotoxin was purified from the venom of *Bungarus multicinctus* as described by Kondo et al. (Kondo et al. 1982a and 1982b). The $β_2$, $β_3$, $β_4$ fractions from CM-Sephadex were pooled, suspended in 70% saturated $(NH_4)_2SO_4$, and loaded on a Phenyl Sepharose column. The bound $β_2$, $β_2$ and $β_4$ was eluted with low salt buffer. The eluate was then passed through an HR 100 column to obtain pure β-bungarotoxin phospholipase (mixture of isoenzymes).

The purified β-bungarotoxin was selectively reduced at pH 5.0, with 100 mM acetate buffer and 50 mM DTT at room temperature for 24 hours.

The reduced β-bungarotoxin mixture was loaded on a mono S column in low salt buffer with 1 mM EDTA pH 4.5, 5 mM sodium acetate, 0.05% 14 Zwittergent. The bound protein was eluted with a gradient of high salt buffer which did not contain detergent but had 2 M NaCl. Pure β-bungarotoxin phospholipase eluted in the gradient between 20–30% high salt buffer.

Phospholipase activity was assay with the spectrophotometric method of de Araújo and Radvanyi (de Araújo and Radvanyi 1987). Specific activity of the purified β-bungarotoxin phospholipase subunit was roughly 10-fold lower than that of the native β-bungarotoxin crude egg white lecithin-cholate micelles, but virtually unchanged on dihexanoyl lecithin under monodisperse conditions. These results imply that while the purified phospholipase subunit probably maintains full enzymatic activity, its ability to bind membranes is partially reduced. Such a reduction may be beneficial to targeting specificity; non-specific membrane affinity would be reduced enhancing diffusion, while in the case of specific binding, the targeting subunit should provide more than ample affinity.

Preparation of sCD4

Soluble CD4 (sCD4) containing 4 domains (amino acid 1–369) was purified as described by Deen et al. (Deen et al. 1988).

Conjugation β-Bungarotoxin Phospholipase to CD4

Purified sCD4 was incubated with sulfo MBS (m-Maleimidobenzene-N-hydroxysulfosuccinimide ester) at pH 7.5 in PBS for thirty minutes. Excess reagent was removed by gel filtration (superose 12). The sulfo MBS activated sCD4 was incubated with β-Bungarotoxin phopholipase (containing a free -SH) at a ratio of 4:1 to produce the SCD4-β-bungarotoxin phospholipase conjugate. The SCD4-β-Bungarotoxin phospholipase was stored in PBS at 4° C.

Test of sCD4-β-Bungarotoxin Phospholipase Conjugate

HIV-1 ($10^5$ infectious units) was mixed with 1 µg/ml of test compound at 37° C. for 2 hours. Test cells were innoculated with the mixture for two hours. The cells were then washed three times with PBS and cultured for six days. The results are shown in Table 3.1:

TABLE 3.1

| (Number of viral particles/ml in control) (Number with drug added) | |
|---|---|
| Test Compound | Inhibition Ratio |
| Control = PBS | 1 |
| + Dextran Sulfate | 1 |
| + Pentosan Sultate | 1 |
| + Conjugate | 10 |

It should be emphasized that this is a very restricted assay. Both dextran sulfate and pentosan sulfate which are accepted standards by which to judge viral inactivation potency (Abrams et al. 1989), at these concentrations (1 µg/ml), do not show significant activation. Even so, the sCD4-β-Bungarotoxin phospholipase conjugate was able to reduce viral production by 10-fold.

REFERENCES

Abe, T., Stefano, A. & Miledi, R. (1977). Isolation and characterization of presynaptically acting neurotoxins from the venom of Bungarus snakes. *Eur. J. Biochem.* 80, 1–12.

Abrams, D. I., S. Kuno, R. Wong, K. Jeffords, M. Nash, J. B. Molaghan, R. Gorter,. and R. Ueno. (1989). Oral dextran sulfate (UA001) in the treatment of the acquired immunodeficiency syndrome (AIDS) and AIDS-related complex. Ann. Intern. Med. 110, 183–188.

Berndt, K. D., Güntert, P., Orbons, L. P. & Wuthrick, K. (1992). Determination of a high-quality nuclear magnetic resonance solution structure of the bovine pancreatic trypsin inhibitor and comparison with three crystal structures. *J. Mol. Biol.* 227, 757–775.

Berndt, K. D., Güntert, P. & Wüthrich, K. (1993). Nuclear magnetic resonance solution structure of dendrotoxin K from the venom of *Dendroaspis polylepis polylepis*. *J. Mol. Biol.* 234, 735–750.

Bidard, J.-N., Mourre, C. & Lazdunski, M. (1987). Two potent central convulsant peptides, a bee venom toxin, the MCD peptide, and a snake venom toxin, dendrotoxin I, known to block K$^+$ channels, have interacting receptor sites. *Biochem. Biophys. Res. Commun.* 143, 383–389.

Bode, W. & Huber, R. (1992). Natural protein proteinase inhibitors and their interaction with proteinases. *Eur. J. Biochem.* 204, 433–451.

Brunie, S., Bolin, J., Gewirth, D. & Sigler, P. B. (1985). The refined crystal structure of dimeric phospholipse A2 at 2.5 Å. Access to a shielded catalytic center. *J. Biol. Chem.* 260, 9742–9749.

Brunger, A. T. (1990). Extension of molecular replacement: a new search strategy based on Patterson correlation refinement. *Acta Crystallogr.* B44, 46–57.

Brunger, A. T. (1992a). XPLOR Manual, Version 3.1. Yale University, New Haven, Conn.

Brunger, A. T. (1992b). Free R value: a novel statistical quantity for assessing the accuracy of crystal structures. *Nature* 355, 472–475.

Cechova, D. (1976). Trypsin inhibitor from cow colostrum. *Methods Enzymol.* 45, 806–813.

Chang, C. C. (1985). Neurotoxins with phospholipase $A_2$ activity in snake venoms. *Proc. Natl. Sci. Counc. B. ROC* 9, 126–142.

Chang, C. C. & Lee, C. Y. (1963). Isolation of neurotoxins from the venom of *Bungarus multicinctus* and their modes of neuromuscular blocking action. *Arch. Int. Pharmocodyn. Ter.* 144, 241–257.

Chen, Z. & Bode W. Refined 2.5 Å X-ray crystal structure of the complex formed by porcine kallikrein A and the bovine pancreatic trypsin inhibitor. Crystallization, comparison with its components and with the bovine trypsin-pancreatic trypsin inhibitor complex. *J. Mol. Biol.* 164, 238–311.

Cherubini, E., Ari, Y. B., Gho, M., Bidard, J. N. & Lazdunski, M. (1987). Long-term potentiation of synaptic transmission in the hippocampus induced by a bee venom peptide. *Nature* 328, 70–73.

Collaborative Computational Project, Number 4 (1994). The CCP4 suite: programs for protein crystallography. *Acta Cryst.* D50, 760–763.

Contrell, G. A., Green, K. A. & Davies, N. W. (1990). The neuropeptide Phe-Met-Arg-Phe-NH2 (FMRFamide) can activate a ligand-gated ion channel in Helix neurones. Pflügers Arch. 416, 612–614.

Danse, J.-M., Toussaint, J.-L. & Kempf, J. (1990a). Nucleotide sequence encoding β-bungarotoxin A2-chain from the venom of *Bungarus multicinctus*. *Nucl. Acid. Res.* 18, 4609.

Danse, J.-M., Garnier, J.-M. & Kempf, J. (1990b). cDNA deduced amino-acid sequence of a new phospholipase from *Bungarus multicinctus*. *Nucl. Acid. Res.* 18, 4610.

de Araújo, A. L. and Radvanyi, F. (1987). Determination of phospholipase $A_2$ activity by a colormetric assay using a pH indicator. *Toxicon*, 25, 1181–1188.

Deen, K. C., McDougal, J. S., Inacker, R., Folena-Wasserman, G., Arthos, J., Rosenberg, J., Maddon, P. J., Axel, R. and Sweet, R. W. (1988). A soluble form of CD4 (T4) protein inhibits AIDS virus infection. *Nature* 331, 82–84.

Deisenhofer, J. & Stiegemann, W. (1975). Crystallographic refinement of structure of bovine pancreatic trypsin inhibitor at 1.5 Å resolution. *Acta Crystallogr.* B31, 238–250.

Delot, E. & Bon, C. (1993). Model for the interaction of crotoxin, a phospholipase $A_2$ neurotoxin, with presynaptic membranes. *Biochem.* 32, 10708–10713.

Dennis, E. A. (1994). Diversity of group types, regulation, and function of phospholipase $A_2$. *J. Biol. Chem.* 269, 13057–13060.

Dijkstra, B. W., Kalk, K. H., Hol, W. G. J. & Drenth, J. (1981). Structure of bovine pancreatic phospholipase $A_2$ at 1.7 Å resolution. *J. Mol. Biol.* 147, 97–123.

Dufton, M. J. (1985). Proteinase inhibitors and dendrotoxins. Sequence classifications, structural prediction and structure/activity. *E. J. Biochem.* 153, 647–654.

Evans, S. V. (1993). SETOR—hardware-lighted 3-dimensional solid model representations of macromolecules. *J. Mol. Graphics* 11, 134–138.

FitzGerald, D. & Pastan, I. (1989). Targeted toxin therapy for the treatment of cancer. *J. Nat. Cancer Inst.* 81, 1455–1463.

Fosset, M., Schmid-Antomarchi, H., Hugues, M., Romey, G. & Lazdunski, M. (1984). The presence in pig brain of an endogenous equivalent of apamin, the bee venom peptide that specifically blocks $Ca^{2+}$-dependent $K^{30}$ channels. *Proc. Natl. Acad. Sci. USA* 81, 7228–7232.

Fremont, D. H., Anderson, D. H., Wilson, I. A., Dennis, E. A. & Xuong, N. H. (1993). Crystal structure of phospholipase A2 from Indian cobra reveals a trimeric association. *Proc. Natl. Acad. Sci. USA* 90, 342–346.

Fuxe, K., Li, X. M., Bjelke, B., Hedlund P. B., Biagini, G. & Agnati L. F. (1994). Possible mechanisms for the powerful actions of neuropeptides. *Ann. N. Y. Acad. Sci.* 739, 42–59.

Harvey, A. L., Anderson, A. J. & Karlsson, E. (1984). Facilitation of transmitter release by neurotoxins from snake venoms. *J. Physiol. Paris* 79, 222–227.

Harvey, A. L., Rowan, E. G., Vatapour, H., Fatehi, M., Castaneda, O. & Karlsson, E. (1994). Potassium channel toxins and transmitter release. *Ann. N. Y. Acad. Sci.* 710, 1–10.

Hendrickson, W. A. & Lattman, E. E. (1970). Representation of phase probability distributions for simplified combination of independent phase information. *Acta Crystallogr.* B26, 136–143.

Ho, C. L., Ko, J. L. & Lee, C. Y. (1986). Differences in pharmacological actions between beta-bungarotoxin and other neurotoxic phospholipases $A_2$ purified from snake venoms. *Proc. Natl. Sci. Counc. B. ROC* 10, 196–202.

Hökfelt, T. (1991). Neuropeptides in perspective: the last ten years. *Neuron* 7, 867–879.

Housset, D., Kim, K. S., Fuchs, J., Woodward, C. & Wlodawer, A. (1991). Crystal structure of a Y35G mutant of bovine pancreatic trypsin inhibitor. *J. Mol. Biol.* 220, 757–770.

Huber, R., Kukla, D., Bode, W., Schwager, P., Bartels, K., Deisenhofer, J. & Steigemann, W. (1974). Structure of the complex formed by bovine trypsin and bovine pancreatic trypsin inhibitor. II. Crystallographic refinement at 1.9 Å resolution. *J. Mol. Biol.* 89, 73–101.

Huber, R., Kukla, D., Ruehlmann, A., Epp, O. & Formanek, H. (1970). Basic trypsin inhibitor of bovine pancreas. 1. Structure-analysis and conformation of polypeptide-chain. *Naturwissen.* 57, 389–392.

Hudson, T. H. & Grillo, F. G. (1991). Brefeldin-A enhancement of ricin A-chain immunotoxins and blockade of intact ricin, modeccin, and abrin. *J. Biol. Chem.* 266, 18586–18592.

Hugues, M., Romey, G., Duval, D., Vincent, J. P. & Lazdunski, M. (1982). Apamin as a selective blocker of the calcium dependent potassium channel in neuroblastoma cells: voltage clamp and biochemical characterization of the toxin receptor. *Proc. Natl. Acad. Sci. USA* 79, 1308–1312.

Hurst, R. S., Busch, A. E., Kavanaugh, M. P., Osborne, P. B., North, R. A. & Adelman, J. P. (1991). Identification of amino acid residues involved in dendrotoxin block of rat voltage-dependent potassium channels. *Mol. Pharm.* 40, 572–576.

Hynes, T. R., Randal, M., Kennedy, L. A., Eigenbrot, C. & Kossiakoff, A. A. (1990). X-ray crystal structure of the protease inhibitor domain of Alzheimer's amyloid b-protein precursor. *Biochem.* 29, 10018–10022.

Joubert, F. J. & Strydom, D. J. (1978). Snake venoms: the amino-acid sequence of trypsin inhibitor E of Dendroaspis polylepis polylepis (Black Mamba) venom. *Eur. J. Biochem.* 87, 191–198.

Joubert, F. J. & Taljaard, N. (1980). The amino acid sequences of two proteinase inhibitor homologues from Dendroaspis angusticeps venom. *Hoppe-Seyler's Z. Physiol. Chem.* 361, 661–674.

Kondo, K., Toda, H., Narita, K. & Lee, C.-Y. (1982a). Amino Acid Sequence of $\beta_2$-bungarotoxin from *Bungarus multicinctus* venom. The amino acid substitutions in the B chains. *J. Biochem.* 91, 1519–1530.

Kondo, K., Toda, H., Narita, K. & Lee, C.-Y. (1982b). Amino Acid Sequences of three $\beta$-bungarotoxins ($\beta_3$-, $\beta_4$-, and $\beta_5$-bungarotoxin) from *Bungarus multicinctus* venom. Amino acid substitutions in the A chains. *J. Biochem.* 91, 1531–1548.

Kraulis, P. (1991). MOLSCRIPT: a program to produce both detailed and schematic plots of proteins. *J. Appl. Crystallogr.* 24, 946–950.

Kuipers, O. P., Thunnissen, M. M. G. M., de Geus, P., Dijkstra, B. W., Drenth, J., Verheij, H. M. & de Haas, G. H. (1989). Enhanced activity and altered specificity of phospholipase $A_2$ by deletion of surface loop. *Science* 244, 82–85.

Kumar, N. V., Wemmer, D. E. & Kallenbach, N. R. (1988). Structure of P401 (mast cell degranulating peptide) in solution. *Biophy. Chem.* 31, 113–119.

Lambeau, G., Schmid-Alliana, A., Lazdunski, M. & Barhanin, J. (1990). Identification and purification of a very high affinity binding protein for toxic phospholipases $A_2$ in skeletal muscle. *J. Biol. Chem.* 265, 9526–9532.

Lancelin, J.-M., Foray, M.-F., Poncin, M., Hollecker, M. & Marion, D. (1994). Proteinase inhibitor homologues as potassium channel blockers. *Nature Struc. Biol.* 1, 246–250.

Laskowski, M. & Kato, I. (1980). Protein inhibitors of proteinases. *Ann. Rev. Biochem.* 49, 593–626.

Maraganore, J. M. & Heinrikson, R. L. (1986). The lysine-49 phospholipase $A_2$ from the venom of *Agkistondon piscivorus piscivorus*. Relation of structure and function to other phospholipases $A_2$. *J. Biol. Chem.* 261, 4797–4804.

McDonald, N. Q. & Kwong, P. D. (1993). Does Noggin head a new class of Kunitz domain? *Trends Biochem. Sci.* 18, 208–209.

Nicholls, A., Sharp, K. A. & Honig, B. (1991). Protein folding and association: insights from the interfacial and thermodynamic properties of hydrocarbons. *Proteins* 11, 281–296.

Pastan, I., V. Chaudhary, and D. J. FitzGerald. (1992). Recombinant toxins as novel therapeutic agents. *Annu. Rev. Biochem.* 61, 331–354.

Petersen, M., Penner, R., Pierau, F.-K. & Deyer, F. (1986). Beta-bungarotoxin inhibits a non-inactivating potassium current in guinea pig dorsal root ganglion neurons. *Neurosci. Lett.* 68, 141–145.

Politi, L. E. & Adler, R. (1986). Generation of enriched populations of cultured photoreceptor cells. *Invest. Ophthal. Visual Science* 27, 656–665.

Ponder, J. W. & Richards, F. M. (1987). Tertiary templates for proteins: use of packing criteria in the enumeration of allowed sequences for different structural classes. *J. Mol. Biol.* 193, 775–791.

Press, O. W. (1991). Immunotoxins. *Biotherapy* 3, 65–76.

Radvanyi, F., Saliou, B., Bon, C. & Strong, P. N. (1987). The interaction between the presynaptic phospholipase neurotoxins $\beta$-bungarotoxin and crotoxin and mixed detergent-phosphatidylcholine micelles. *J. Biol. Chem.* 262, 8966–8974.

Rehm, H. & Betz, H. (1984). Solubilization and characterization of the beta-bungarotoxin-binding protein of chick brain membranes. *J. Biol. Chem.* 259, 6865–6869.

Rehm, H. & Tempel, B. L. (1991). Voltage-gated $K^+$ channels of the mammalian brain. *FASEB J.* 15, 164–170.

Schmidt, T., Stumm-Zollinger, E., Chen, P.-S., Böhlen, P. & Stone, S. R. (1989). A male accessory gland peptide with protease inhibitory activity in *Drosophila funebris*. *J. Biol. Chem.* 264, 9745–9749.

Schweitz, H., Heurteaux, C., Bois, P., Moinier, D., Romey, G. & Lazdunski, M. (1994). Calcicludine, a venom peptide of the Kunitz-type protease inhibitor family, is a potent blocker of high-threshold $Ca^{2+}$ channels with a high affinity for L-type channels in cerebellar granule neurons. *Proc. Natl. Acad. Sci. USA* 91, 878–882.

Scott, D. L., White, S. P., Otwinowski, Z., Yuan, W., Gelb, M. H. & Sigler, P. B. (1990). Interfacial catalysis: the mechanism of phospholipase $A_2$. *Science* 250, 1541–1546.

Siegall, C. B. 1994. Targeted toxins as anticancer agents. *Cancer.* 74, 1006–1012.

Skarzynski, T. (1992). Crystal strucuture of $\alpha$-dendrotoxin from the green mamba venom and its comparison with the structure of bovine pancreatic trypsin inhibitor. *J. Mol. Biol.* 224, 671–683.

Smith, W. C. & Harland, R. M. (1992). Expression cloning of noggin, a new dorsalizing factor localized to the Spemann organizer in Xenopus embryos. *Cell* 70, 829–840.

Smith, L. A., Lafaye, P. J., LaPenotiere, H. F., Spain, T. & Dolly, J. O. (1993). Cloning and functional expression of Dendrotoxin K from Black Mamba, a $K^+$ channel blocker. *Biochem.* 32, 5692–5697.

Stocker, M., Pongs, O., Hoth, M., Heinemann, S. H., Stuhmer, W., Schroter, K.-H. & Ruppersberg, J. P. (1991). Swapping of functional domains in voltage-gated $K^+$ channels. *Proc. R. Soc. Lond.* 245, 101–107.

Strydom, D. J. (1976). Snake venom toxins: purification and properties of low-molecular-weight polypeptides of *Dendroaspis polylepis polypepis* (Black Mamba) venom. *Eur. J. Biochem.* 69, 169–176.

Tschesche, H. & Dietl, T. (1975). The amino-acid sequence of isoinhibitor K from snails (*Helix pomatia*). A sequence determination by automated Edman degradation and mass-spectral identification of the phenylthiohydantoins. *Eur. J. Biochem.* 58, 439–451.

Vernon, L. P., and J. D. Bell. (1992). Membrane structure, toxins and phospholipase $A_2$ activity. Pharmacol. Ther. 54, 269–295.

Westerlund, B., Nordlund, P., Uhlin, U., Eaker, D. & Eklund, H. (1992). The three-dimensional structure of notexin, a presynaptic neurotoxic phospholipase A$_2$ at 2.0 Å resolution. *Fed. Eur. Biochem. Soc.* 301, 159–164.

Woolley, P., and Petersen, S. V., (1994) Lipases: Their structure, biochemistry and application, Cambridge University Press, Cambridge, UK. Woolley and Peterson, eds.

What is claimed is:

1. A non-naturally occurring targeted lipolytic composition consisting essentially of a phospholipase subunit of β-bungarotoxin covalently linked to a soluble CD4 molecule, wherein said composition preferentially recognizes human immunodeficiency virus and inactivates said virus upon contact therewith in vitro.

2. A method of inactivating a human immunodeficiency virus which comprises contacting the virus in vitro with a concentration of the composition of claim 1 effective to inactivate the virus.

* * * * *